United States Patent [19]

Phillips et al.

[11] 4,212,983
[45] Jul. 15, 1980

[54] MANUFACTURE OF IMIDAZOLINE COMPOUNDS

[75] Inventors: Brinley M. Phillips, Whitehaven; Robert B. Lace, Egremont; Alan J. Lambie, Whitehaven, all of England

[73] Assignee: Albright & Wilson Limited, Oldbury, England

[21] Appl. No.: 971,449

[22] Filed: Dec. 20, 1978

[30] Foreign Application Priority Data

Dec. 22, 1978 [GB] United Kingdom ............... 53575/78

[51] Int. Cl.² .................. C07D 233/14; C07D 233/16
[52] U.S. Cl. ..................................... 548/352; 548/347
[58] Field of Search ......................... 548/352, 347, 354

[56] References Cited

U.S. PATENT DOCUMENTS

| | | | |
|---|---|---|---|
| 2,155,877 | 4/1939 | Waldmann | 548/347 |
| 2,215,864 | 9/1940 | Waldmann | 548/352 |
| 2,267,965 | 12/1941 | Wilson | 548/352 |
| 2,268,273 | 12/1941 | Wilkes et al. | 548/352 |
| 2,355,837 | 8/1944 | Wilson | 548/352 |
| 2,528,378 | 10/1950 | Mannheimer | 548/354 |
| 2,992,230 | 7/1961 | Lescisin | 548/347 |
| 3,408,361 | 10/1968 | Mannheimer | 548/352 |
| 3,555,041 | 1/1971 | Katz | 548/352 |

FOREIGN PATENT DOCUMENTS

| | | | |
|---|---|---|---|
| 2615886 | 10/1977 | Fed. Rep. of Germany | 548/347 |
| 1243868 | 8/1971 | United Kingdom | 260/153 |
| 1317741 | 5/1973 | United Kingdom | 548/352 |

*Primary Examiner*—Natalie Trousof
*Attorney, Agent, or Firm*—Frishauf, Holtz, Goodman & Woodward

[57] ABSTRACT

The invention provides a process for reducing the diamide content of imidazolines having the formula:

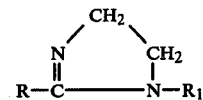

wherein R represents an aliphatic group having from at least 4 carbon atoms and $R_1$ represents an alkyl or alkenyl group having from 1 to 4 carbon atoms.

The mixture of imidazoline and diamide is reacted with a primary or secondary amine which deacylates the diamide to an amido-amine. The product of this deacylation is an imidazoline solution which remains clear even on prolonged storage.

The imidazoline is produced by reaction of an acid RCOOH with a diamine $NH_2(CH_2)_2 NHR_1$. Preferably this diamine is used as the deacylating agent.

11 Claims, No Drawings

MANUFACTURE OF IMIDAZOLINE COMPOUNDS

This invention relates to a process for the manufacture of imidazolines containing small amounts of diamide impurity by the reaction between a fatty acid and a diamine. Imidazolines which are substituted in the two position by an aliphatic group comprising a minimum of four carbon atoms are used as intermediates in the production of a variety of derivatives which are valuable surface active agents. Many of these derivatives exhibit an especially mild action on the skin and have been widely employed as ingredients of shampoos and other clensing compositions which come into intimate contact with the skin.

The imidazolines with which this invention is concerned are those having the formula:

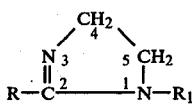

wherein R represents an aliphatic group comprising at least four carbon atoms and $R_1$ represents a substituted or unsubstituted alkyl or alkenyl group comprising from 1 to 4 carbon atoms. The inset numerals define the substituent groups on the ring in the manner which will be adopted for the purposes of this disclosure.

The production of these imidazolines by the reaction between a fatty acid of the formula:

RCOOH and a diamine of the formula:

has been described in U.S. Pat. Nos. 2,267,965 and 2,528,378. The desired reaction can be represented as proceeding according to the sequential equations:

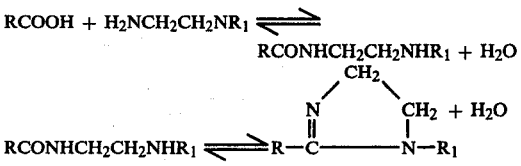

A problem which arises when carrying out this reaction is the formation of a diamide by-product by a reaction between the amido-amine product by the reaction shown as equation (1) and a further molecule of a fatty acid according to the equation:

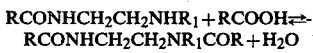

Where the reaction is carried out using equimolar quantites of diamine and fatty acid as in U.S. Pat. No. 2,528,378 the product imidazoline is contaminated with small but significant quantities of diamide. The diamides are present in the intermediate imidazolines and may be shed from solution after the imidazoline is converted into its water soluble surfactant derivatives after or even prior to its incorporation into a cleansing composition. Upon prolonged storage the appearance of the product changes from that of a clear liquid to that of a cloudy one due to the separation of the diamide. A product having such a cloudy appearance is less acceptable to the public.

U.S. Pat. No. 3,408,361 described a process reacting a fatty acid with a diamine so as to minimise the formation of diamide.

Essentially this process involves the maintenance of an excess of diamine substantially throughout the course of the reaction. While such procedures effectively reduce the quantity of diamide formed to an acceptable level they involve careful monitoring of the reaction, the benefits of which are negated if by error the excess of diamine is used up at one point in the reaction.

We have now discovered that if an imidazoline product which is contaminated with diamide is heated in the presence of a suitable deacylating agent the amido-amine intermediate is formed and may react further to form the imidazoline. In particular the deacylating agent is a primary or secondary amine of the formula:

wherein at least one of $R_2$ or $R_3$ represents an alkyl or alkenyl group comprising from 1 to 4 carbon atoms and the other represents a hydrogen atom or such an alkyl or alkenyl group.

Our process comprises heating the diamide containing imidazoline in the presence of a primary or secondary amine at an elevated temperature below that at which the amine is removed from the reaction mixture, so as to reduce the diamide contents thereof. The novel processes lead to a slightly increased yield of imidazoline in which the diamide content can be reduced to as little as 0.1% by weight. Sufficient amine to achieve this reduction will be employed and any excess may be stripped from the product in a conventional manner. Such techniques enable the reaction of the fatty acid with the diamine to be carried out under less rigorously monitored conditions. In the preferred case they enable equimolar quantities of the diamine and acid to be reacted, the product being subsequently heated with an amine so as to reduce the quantity of diamide present to an acceptable level. It is believed that the amine reacts with the undesired diamide to regenerate the monoamido-amine and a monoamide. The monoamido-amine apparently reacts according to the above equation (2) to generate the desired imidazoline. The second product of the reaction, the mono-amide does not detract from the properties of the imidazoline or any product and composition derived therefrom since it forms derivatives which are water soluble or which at least are not shed from aqueous solutions of imidazoline derivatives.

Thus from one aspect our invention provides a process for the production of an imidazoline of low diamide content which comprises heating a preformed mixture comprising an imidazoline of the formula:

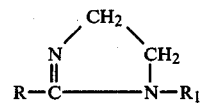

and a diamide of the formula:

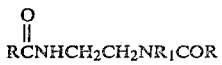

with an amine of the formula:

R$_2$R$_3$NH wherein R represents an aliphatic group having at least four carbon atoms, R$_1$ represents a substituted or unsubstituted alkyl or alkenyl group having from 1 to 4 carbon atoms, R$_2$ represents a substituted or unsubstituted aliphatic group having from 1 to 4 carbon atoms and R$_3$ represents any of the groups R$_2$ or a hydrogen atoms, at a temperature of at least 150° C.

The primary or secondary amine used as the deacylating agent is selected so that the mono-amide into which it is converted is compatible with the imidazoline and can be incorporated into a cleansing composition without conferring any deleterious properties. In general R$_2$ and R$_3$ will represent substituted or unsubstituted alkyl groups e.g. methyl ethyl n or iso propyl n, iso or tertiary butyl groups preferably those groups containing 1 or 2 carbon atoms.

The use of secondary amines is preferred and in particular those in which R$_2$ and R$_3$ contain an amino or hydroxyl substituent. In general, it is most convenient and preferable to employ a diamine as the deacylating agent in particular the diamine employed in the production of the imidazoline i.e. the compound of the formula:

Such deacylating agents are themselves acylated in the course of the reaction to yield amido-amines which may undergo dehydration to form an imidazoline. This is valuable in that this 'by-product' forms a useful part of the desired product and may be identical with it and at least is extremely unlikely to cause any problems of compatibility.

The use of such diamines as deacylating agents is strongly preferred where the mixture comprises relatively large proportions of diamide e.g. 10% as otherwise the yield of the desired imidazoline based upon the quantities of acid and diamine used to produce the contaminated imidazoline will be unnecessarily reduced.

The novel processes of the invention find particular application to mixtures of imidazoline and diamide produced by the reaction of substantially equimolar quantites of fatty acid and diamine e.g. as described in U.S. Pat. No. 2,528,378. The product of such procedures comprises unacceptably high quantities of diamide but the procedure itself offers the advantage of not requiring close monitoring and efficient utilisation of the diamine. The subsequent application of our novel process retains these advantages whilst giving a product of low diamide content.

The preferred fatty acids for use in such processes are those in which R represents an alkyl, alkenyl or cycloalkyl group comprising from 8 to 22 carbon atoms. Conveniently such acids are obtained from natural sources and comprise mixtures of acids in which the nature of the group R varies. Suitable acids include caproic, heptylic, heptanoic, caprylic, undecylic, lauric, palmitic, stearic, isostearic, ethylhexanoic, behenic, arachic, cerotic, oleic erucic, linoleic, linolenic and ricinoleic acids.

Natural mixtures useful include the so-called coconut acids, palm oil acids and tallow acids.

Preferably such acids comprise an average of from 10 to 18 most preferably 12 to 14 carbon atoms per molecule.

The diamine reactants preferred for present use are those wherein R$_1$ represents a alkyl, hydroxy alkyl or amino alkyl group having from 1 to 4 carbon atoms e.g. a methyl, ethyl, n or iso propyl, n, iso or tertiary butyl group or a hydroxy or amino substituted derivative thereof. Preferably R$_1$ represents a mono-hydroxy substituted alkyl group having from 2 to 4 carbon atoms. Most preferably R$_1$ represents a hydroxy ethane group —CH$_2$CH$_2$OH. The most preferred diamine from which the imidazoline is derived is N-(2-aminoethyl)-ethanolamine.

The reaction between the fatty acid and the diamine is carried out using conventional techniques. In the preferred embodiment in which a high diamide content imidazoline product is produced the fatty acid and 1 to 1.05 moles of a diamine per mole of the acid are charged to a suitable vessel from which air is excluded and the temperature raised to a value of from 140° to 200° C. During or after this temperature increase the pressure is reduced to effect a rapid evolution of water from the system. The reaction is terminated when more than 1.90 moles of water per mole of acid have been evolved. The product mixture comprises an imidazoline together with at least 2% and normally from 2 to 10% by weight of a diamide.

The deacylating agent (the amine) is added to this produce mixture in sufficient quantities to react with all the diamide present. Conveniently a large excess is employed as all the unchanged amine can be stripped from the product at the end of the reaction and recycled. The temperature of the mixture is then raised to and maintained at a value above 150° C. but below the boiling point of the amine. Preferably, the temperature is maintained at a value of from 180° to 250° C. more preferably 180° to 220° C. whilst the vessel is maintained under reflux. The quantity of diamide which is reformed is dependant upon the period for which this elevated temperature is maintained. In general it will be desirable to reduce the diamide content of the imidazoline product to less than 2% by weight and this is usually attained by maintaining the elevated temperatures for periods of from 2 to 6 hours. Our process enables the diamide content to be reduced to very low levels 0.05 percent by weight or less when the higher temperatures and longer heating times are employed.

Any excess amine is stripped from the product, conveniently be reducing the pressure in the vessel.

The procedure outlined above can be carried out as a batch procedure or on a continuous basis. Conveniently, in the case of a continuous process the reaction between a fatty acid and a diamine is carried out in one vessel and the product comprising an imidazoline contaminated with some diamide is allowed to overflow into a second vessel. The deacylating agent is then fed to this second vessel again in large excess the residence time being such as to reduce the diamide content to a satisfactory level. The excess amine can then be stipped off in a stripping column to give the desired product.

The invention is illustrated by the following examples:

EXAMPLE 1

878 g (8.74 moles) of aminoethylethanolamine was charged to a 5 liter flask and heated with stirring to 50° C. 1640 g (8.0 moles) of coconut fatty acid was added, keeping the reaction mixture at a temperature no greater than 60° C. by cooling. The pressure was then reduced to 200 mm Hg abs., and the temperature raised to 140° C. The reactants were then heated to 190° C. at a rate of 20° C./hr. When the temperature of the reactants reached 160° C., the pressure was reduced to 100 mm Hg abs. over a three hour period. The pressure was then reduced to 1 mm Hg abs. During the reaction 15 moles water were removed, and the imidazoline was found to containe 2.2% diamide. 682.5 g (2.5 moles) of the above imidazoline was refluxed under reduced pressure with 78 g (0.15 moles) of aminoethylethanolamine at 90° C. for 5 hours. The pressure was then reduced to 1 mm Hg abs. to strip off the excess amine. The final imidazoline contained 0.7% diamide.

EXAMPLE 2

472.7 g (4.5 moles) of aminoethylethanolamine was charged to a 2 liter flask, and heated with stirring to 50° C. 922.5 g (4.5 moles) of coconut fatty acid was added, maintaining the temperature below 60° C. by cooling. The pressure was then reduced to 200 mm Hg abs. and the temperature was raised to 140° C. The reactants were then heated to 190° C. The reactants were then heated to 190° C. at a rate of 20° C./hr. When the temperature of the reactants reached 160° C. the pressure was reduced to 10 mm Hg abs. over a 2½ hour period. The imidazoline was found to contain 3.9% diamide. 410 g (1.5 moles) of the imidazoline, was refluxed under reduced pressure with 31.6 g (0.3 moles) of aminoethylethanolamine at 190° C. for 4 hours. The pressure was then reduced to strip off the excess amine. The final imidazoline contained 0.9% diamide.

EXAMPLE 3

Preparation of Coconut Imidazoline

A 2 l flask was charged with 419 g (4 m) aminoethylethanolamine and 820 g (4 M) coconut fatty acid was added with stirring at 50° to 60° C. The pressure was reduced to 200 mm Hg abs. and the reactants were heated to 140° C. The temperature was then increased to 220° C. at a rate of 20° C./hr. and the pressure was then reduced to 15 mm over 3 hours. During the reaction 134.3 g (7.5 M) water was recovered together with 14.3 g amine. The imidazoline was analysed and found to contain 2.5% diamide.

23.7 g (0.23 M) aminoethylethanolamine was added to 1040 g of this product (=3.8 moles fatty acid in the original charge). The mixture was refluxed for 5 hours at 220° C. under vacuum (55 mm Hg abs.) and the pressure was then reduced to 4 mm Hg abs. to distil off excess aminoethylethanolamine. The imidazoline was analysed and found to contain 0.8% diamide.

EXAMPLE 4

Preparation of Lauric Imidazoline

A 2 l flask was charged with 306.1 g (2.9 mol) aminoethylethanolamine and 585 g lauric acid (2.9 mol) was added with stirring at 50° to 60° C. The pressure was reduced to 200 mm Hg abs. and the reactants were heated to 140° C. The temperature was then increased to 220° C. at a rate of 20° /hr. and the pressure was then reduced to 15 mm Hg abs. over 3 hours. During the reaction 96.6 g water (5.4 mol) were recovered together with 9.9 g aminoethylethanolamine. The imidazoline was analysed and found to contain 4.1% diamide.

17.1 g (0.16 mol) aminoethylethanolamine was added to 734 g of this product (=2.74 mols fatty acid in the original charge). The mixture was refluxed for 5 hours at 220° C. under vacuum (50 mm Hg.abs.).

Finally, excess aminoethylethanolamine was distilled off by reducing the pressure to 2 mm Hg. abs. The imidazoline was analysed and found to contain 1.5% diamide.

What we claim is:

1. A process for the production of an imidazoline of low diamide content which comprises heating a preformed mixture comprising an imidazoline of formula:

$$\begin{array}{c} \phantom{R-}CH_2 \\ N \diagup \phantom{xx} \diagdown CH_2 \\ \| \phantom{xxxxxxx} | \\ R-C\text{------}N-R_1 \end{array}$$

and a diamide of the formula $$\overset{O}{\underset{\|}{R C}}NHCH_2CH_2NR_1COR$$

with an amine of the formula $$R_2R_3NH$$

wherein
  R represents an alkyl, alkenyl or cycloalkyl group having from 8 to 22 carbon atoms,
  $R_1$ represents an alkyl or alkenyl group having from 1 to 4 carbon atoms or one of said groups containing a hydroxy or an amino substituent,
  $R_2$ represents an aliphatic group having from 1 to 4 carbon atoms or such an aliphatic group containing an amino or hydroxy substituent, and
  $R_3$ represents any of the groups $R_2$ or a hydrogen atom,
at a temperature of at least 150° C.

2. A process according to claim 1, wherein $R_2$ and $R_3$ represent alkyl, hydroxy alkyl or amino alkyl groups having from 1 to 4 carbon atoms.

3. A process according to claim 2, wherein $R_2$ represents an amino ethyl group having the formula —$CH_2CH_2NH_2$ and $R_3$ is identical with the group $R_1$.

4. A process according to claim 2, wherein $R_1$ represents a monohydroxy substituted alkyl group having from 1 to 4 carbon atoms.

5. A process according to claim 4, wherein $R_1$ represents a hydroxy ethane group.

6. A process according to claim 2, wherein R represents an alkyl, alkenyl or cycloalkyl group having from 10 to 18 carbon atoms.

7. A process according to claim 2, wherein R represents an alkyl, alkenyl or cycloalkyl group having from 12 to 14 carbon atoms.

8. A process according to claim 1 or claim 3, wherein the imidazoline and diamide are heated with the amine at a temperature of from 180° to 250° C.

9. A process according to claim 1, wherein the temperature is in the range 180° to 220° C.

10. A process according to claim 3, wherein R represents an alkyl, cycloalkyl or alkenyl group having from 10 to 18 carbon atoms.

11. A process according to claim 3 or claim 7, wherein the imidazoline and diamide are heated with the amine at a temperature of from 180° to 220° C.

* * * * *